(12) United States Patent
Riley et al.

(10) Patent No.: US 10,988,675 B2
(45) Date of Patent: Apr. 27, 2021

(54) METHOD TO HYDRAULICALLY FRACTURE A WELL (71) Applicant: Multi-Chem Group, LLC, San Angelo, TX (US)

(72) Inventors: Howard Thomas Riley, Jefferson Hills, PA (US); Teddy Joel Dubois, Canonsburg, PA (US); James William Ogle, Livingston, TX (US)

(73) Assignee: Multi-Chem Group, LLC, Houston, TX (US)

( * ) Notice: Subject to any disclaimer, the term of this patent is extended or adjusted under 35 U.S.C. 154(b) by 0 days.

(21) Appl. No.: 16/234,178

(22) Filed: Dec. 27, 2018

(65) Prior Publication Data

US 2019/0153303 A1    May 23, 2019

Related U.S. Application Data

(63) Continuation-in-part of application No. 16/026,335, filed on Jul. 3, 2018.

(60) Provisional application No. 62/588,641, filed on Nov. 20, 2017.

(51) Int. Cl.
| | | |
|---|---|---|
| *E21B 43/26* | (2006.01) | |
| *C09K 8/68* | (2006.01) | |
| *B01F 15/00* | (2006.01) | |
| *G01N 21/31* | (2006.01) | |
| *G01N 33/18* | (2006.01) | |
| *B01F 3/08* | (2006.01) | |

(52) U.S. Cl.
CPC .............. *C09K 8/68* (2013.01); *B01F 3/0803* (2013.01); *B01F 15/00227* (2013.01); *B01F 15/00233* (2013.01); *B01F 15/00344* (2013.01); *G01N 33/182* (2013.01); *B01F 2215/0081* (2013.01); *C09K 2208/28* (2013.01)

(58) Field of Classification Search
None
See application file for complete search history.

(56) References Cited

U.S. PATENT DOCUMENTS

| | | |
|---|---|---|
| 4,014,736 A | 3/1977 | Sexton |
| 5,005,406 A | 4/1991 | Jasinksi et al. |
| 7,579,302 B2 | 8/2009 | Mechan et al. |
| 9,256,701 B2 | 2/2016 | Chen et al. |
| 9,423,326 B1 | 8/2016 | Fares et al. |
| 2004/0018936 A1 | 1/2004 | Hammel et al. |
| 2004/0101457 A1 | 5/2004 | Pahlman et al. |
| 2004/0221660 A1 | 11/2004 | Dutton et al. |

(Continued)

FOREIGN PATENT DOCUMENTS

WO    2007068876    6/2007

OTHER PUBLICATIONS

International Search Report and Written Opinion for Application No. PCT/US2019/053893 dated Jan. 10, 2020.

(Continued)

*Primary Examiner* — Charles R Nold
(74) *Attorney, Agent, or Firm* — Tenley Krueger; C. Tumey Law Group PLLC (57) ABSTRACT

A method may include: determining a total dissolved solids (TDS) concentration of a water source; correlating the TDS concentration to an ion concentration; and selecting at least one friction reducing polymer for a hydraulic fracturing operation based at least in part on the ion concentration.

20 Claims, 6 Drawing Sheets

(56) References Cited

U.S. PATENT DOCUMENTS

| | | |
|---|---|---|
| 2009/0105097 A1 | 4/2009 | Abad et al. |
| 2009/0298721 A1 | 12/2009 | Robb et al. |
| 2011/0132815 A1 | 6/2011 | Angelilli et al. |
| 2012/0018148 A1 | 1/2012 | Bryant et al. |
| 2012/0024525 A1* | 2/2012 | Svarczkopf .............. C09K 8/62 166/267 |
| 2013/0025867 A1 | 1/2013 | Sun et al. |
| 2016/0017203 A1* | 1/2016 | Frederick ................. C09K 8/36 166/308.3 |
| 2019/0153302 A1 | 5/2019 | Straffin et al. |
| 2019/0153303 A1 | 5/2019 | Riley et al. |

OTHER PUBLICATIONS

Tomson, R. C. et al, "Development of a Universal Ranking for Friction Reducer Performance", Society of Petroleum Engineers, 2017.

Liebermann, T. D. et al, "User's Manual for Estimation of Dissolved-Solids Concentrations and Loads in Surface Water", U.S. Geological Survey Water-Resources Investigations Report 86-4124, 1987.

USPTO Office Action for U.S. Appl. No. 16/026,335 dated Jun. 24, 2020.

Xu et al, "Case Study: A New Salt-Tolerant Friction Reduer System Enables 100% Re-use of Produced Water in the Marcellus Shale", Society of Petroleum Engineers, 2016.

\* cited by examiner

METHOD TO HYDRAULICALLY FRACTURE A WELL

CROSS-REFERENCE TO RELATED APPLICATIONS

The present application is a continuation-in-part of U.S. patent application Ser. No. 16/026,335, filed on Jul. 3, 2018, which claims priority to U.S. Provisional Application No. 62/588,641, filed on Nov. 20, 2017, the entire disclosures of which are incorporated herein by reference.

BACKGROUND

Hydrocarbon-producing wells are often stimulated by hydraulic fracturing operations, wherein proppants may be used to hold open or "prop" open fractures created during high-pressure pumping. Once the pumping-induced pressure is removed, proppants may prop open fractures in the rock formation and thus preclude the fracture from closing. As a result, the amount of formation surface area exposed to the well bore may be increased, enhancing hydrocarbon recovery rates.

An important component of hydraulic fracturing fluids is a friction reducing polymer. Pumping rates for hydraulic fracturing operations may regularly exceed 50 barrels per minute (8 m$^3$/min) or more, which may cause turbulence in conduits such as wellbore tubing, liners, and casings. Turbulent flow of hydraulic fracturing fluid decreases the pressure of the fluid as it flows through conduits leading to high horsepower requirements to maintain pressure and flow rates. Some common friction reducing polymers may include long chain water soluble polymers which may aid in moderating turbulence by reducing eddy currents within a conduit.

A friction reducing polymer may be selected for a particular hydraulic fracturing fluid based at least in part on quality and properties of water available to create the hydraulic fracturing fluid at a well site. Oftentimes water is available from drilled water wells, surface water such as lakes and ponds, or seawater. Water from these and other sources may contain dissolved solids such as salts and metals as well as other chemical species. The friction reducing polymer may be significantly affected by the concentration of dissolved solids. In general, a relatively higher dissolved solids concentration may cause adverse effects with hydration and stability of a given friction reducing polymer as compared to a relatively lower dissolved solids concentration. The effects may be exacerbated at relatively higher concentrations of dissolved solids to the point where the friction reducing polymer is no longer performing to reduce turbulence within the hydraulic fracturing fluid. In extreme instances, the friction reducing polymer may phase-separate from the bulk aqueous phase to form fish-eye nodules of un-hydrated polymer.

There may be a wide variety of friction reducing polymers that may be included in hydraulic fracturing fluids for a particular use. Some friction reducing polymers may be designed to be operable in fluids that contain relatively higher total dissolved solids content example. These severe duty friction reducing polymers may be more expensive than friction reducing polymers that are not designed to be operable in relatively higher total dissolved solids fluids. The chosen friction reducing polymer for making a fracturing fluid may be a function of total dissolved solids level of the base aqueous fluid and of the price of the friction reducing polymer.

An operator or oilfield service company may design the hydraulic fracturing fluid based at least in part on tests performed on the water at the well site. The water may be tested at least once before the hydraulic fracturing fluid is designed. A friction reducing polymer may then be selected that would have the necessary performance with the properties of the water as tested. However, there exist challenges when the water quality changes between fracturing stages or during a particular fracturing stage. For example, if the total dissolved solids increases to a point where the selected friction reducing polymer is ineffective, the hydraulic fracturing system may not be able to deliver the fracturing fluid to the formation at a rate and pressure to keep extending existing fractures and creating new fractures. The pressure exerted by the fracturing fluid may fall below the closing pressure of the formation and the hydraulic fracturing operation may cease. Alternatively, if the total dissolved solids decreases, the selected friction reducing polymer may not be the most cost effective friction reducing polymer to use thereby unnecessarily increasing the cost of the hydraulic fracturing operation.

BRIEF DESCRIPTION OF THE DRAWINGS

These drawings illustrate certain aspects of the present disclosure, and should not be used to limit or define the disclosure.

DETAILED DESCRIPTION

The present disclosure may relate to subterranean operations, and, in one or more implementations, to hydraulic fracturing methods including performing real-time water quality analysis and correlating the water quality analysis with archival data to determine a total dissolved solids concentration of the water. A friction reducing polymer and a concentration thereof may be selected based on the total dissolved solids concentration to provide a fracturing fluid with a lower cost while maintaining friction reducing properties. In an example, the friction reducing polymer may be switched from a relatively higher cost friction reducing polymer to a relatively lower cost friction reducing polymer when the total dissolved solids concentration changes from relatively higher to relatively lower.

A hydraulic fracturing fluid may include an aqueous base fluid, a proppant, and a friction reducing polymer. The aqueous based fluid may include fresh water, produced water, salt water, surface water, or any other suitable water. The term "salt water" is used herein to mean unsaturated salt solutions and saturated salt solutions including brines and seawater. The aqueous base fluid may include dissolved species of salts and metals that make up the total dissolved solids (TDS) count for a particular sample of aqueous base fluid. Examples of dissolved species may include, but are not limited to, fluoride (F−), Calcium (Ca2+), Chloride (Cl−), Iodide (I−), Cupric (Cu2+), Bromide (Br−), Silver (Ag+), Lithium (Li+), Magnesium (Mg2+), Potassium (K+), Sodium (Na+), polyatomic ions such as Nitrates (NO3−), Nitrites (NO2−), Fluoroborate (BF4−), Ammonium (NH4+), Perchlorate (ClO4−), salts of and elemental forms of metals such as lithium, sodium, potassium, beryllium, magnesium, calcium, strontium, iron, zinc, manganese, molybdenum, arsenic, barium, boron, chromium, selenium, uranium, sulfur in the form of sulfides, sulfates, and hydrogen sulfide, and sulfates, and combinations thereof. One of ordinary skill in the art will understand that the present list of dissolved species is not exhaustive of all possible species dissolved in a particular sample of water. Furthermore, one of ordinary skill in the art will understand that for a particular friction reducing polymer, there may be a subset of dissolved species that may affect hydration and performance of the friction reducing polymer and therefore be of particular interest when using the friction reducing polymer in a fracturing fluid.

The water may be present in any amount by weight suitable for a particular hydraulic fracturing application. For example, without limitation, the water may be present at a point ranging from about 50 wt. % to about 100 wt. % based on a total weight of the hydraulic fracturing fluid. Alternatively, at a point ranging from about 50 wt. % to about 60 wt. %, at a point ranging from about 60 wt. % to about 70 wt. %, at a point ranging from about 70 wt. % to about 80 wt. %, at a point ranging from about 80 wt. % to about 90 wt. %, or at a point ranging from about 90 wt. % to about 100 wt. %. One of ordinary skill in the art with the benefit of this disclosure should be able to select an appropriate weight percent of water for a particular hydraulic fracturing fluid.

The hydraulic fracturing fluid may include a proppant. Proppants may include a collection of solid particles that may be pumped into the subterranean formation, such that the solid particles hold (or "prop") open the fractures generated during a hydraulic fracturing treatment. The proppant may include a variety of solid particles, including, but not limited to, sand, bauxite, ceramic materials, glass materials, polymer materials, polytetrafluoroethylene materials, nut shell pieces, cured resinous particulates including nut shell pieces, seed shell pieces, cured resinous particulates including seed shell pieces, fruit pit pieces, cured resinous particulates including fruit pit pieces, wood, composite particulates, and combinations thereof. Suitable composite particulates may include a binder and a filler material wherein suitable filler materials include silica, alumina, fumed carbon, carbon black, graphite, mica, titanium dioxide, meta-silicate, calcium silicate, kaolin, talc, zirconia, boron, fly ash, hollow glass microspheres, solid glass, and combinations thereof. The proppant may have any suitable particle size for a particular application such as, without limitation, nano particle size, micron particle size, or any combinations thereof. As used herein, the term particle size refers to a d50 particle size distribution, wherein the d50 particle size distribution is the value of the particle diameter at 50% in the cumulative distribution. The d50 particle size distribution may be measured by particle size analyzers such as those manufactured by Malvern Instruments, Worcestershire, United Kingdom. As used herein, nano-size is understood to mean any proppant with a d50 particle size distribution of less than 1 micron. For example, a proppant with a d50 particle size distribution at point ranging from about 10 nanometers to about 1 micron. Alternatively, a proppant with a d50 particle size distribution at point ranging from about 10 nanometers to about 100 nanometers, a proppant with a d50 particle size distribution at point ranging from about 100 nanometers to about 300 nanometers, a proppant with a d50 particle size distribution at point ranging from about 300 nanometers to about 700 nanometers, a proppant with a d50 particle size distribution at point ranging from about 700 nanometers to about 1 micron, or a proppant with a d50 particle size distribution between any of the previously recited ranges. As used herein, micron-size is understood to mean any proppant with a d50 particle size distribution at a point ranging from about 1 micron to about 1000 microns. Alternatively, a proppant with a d50 particle size distribution at point ranging from about 1 micron to about 100 microns, a proppant with a d50 particle size distribution at point ranging from about 100 microns to about 300 microns, a proppant with a d50 particle size distribution at point ranging from about 300 microns to about 700 micron, a proppant with a d50 particle size distribution at point ranging from about 700 microns to about 1000 microns, or a proppant with a d50 particle size distribution between any of the previously recited ranges.

Alternatively, proppant particle sizes may be expressed in U.S. mesh sizes such as, for example, 20/40 mesh (212 μm-420 μm). Proppants expressed in U.S. mesh sizes may include proppants with particle sizes at a point ranging from about 8 mesh to about 140 mesh (106 μm-2.36 mm). Alternatively a point ranging from about 16-30 mesh (600 μm-1180 μm), a point ranging from about 20-40 mesh (420 μm-840 μm), a point ranging from about 30-50 mesh (300 μm-600 μm), a point ranging from about 40-70 mesh (212 μm-420 μm), a point ranging from about 70-140 mesh (106 μm-212 μm), or alternatively any range there between. The standards and procedures for measuring a particle size or particle size distribution may be found in ISO 13503, or, alternatively in API RP 56, API RP 58, API RP 60, or any combinations thereof.

Proppants may include any suitable density. In some examples, proppants may have a density at a point ranging from about 1.25 g/cm$^3$ to about 10 g/cm$^3$. Proppants may include any shape, including but not limited, to spherical, toroidal, amorphous, planar, cubic, or cylindrical. Proppants may further include any roundness and sphericity. Proppant may be present in the fracturing fluid in any concentration or loading. Without limitation, the proppant may be present a point ranging from about 0.1 pounds per gallon ("lb/gal") (12 kg/m$^3$) to about 14 lb/gal (1677 kg/m$^3$). Alternatively, a point ranging from about 0.1 lb/gal (12 kg/m$^3$) to about 1 lb/gal (119.8 kg/m$^3$), a point ranging from about 1 lb/gal (119.8 kg/m$^3$) to about 3 lb/gal (359.4 kg/m$^3$), a point ranging from about 3 lb/gal (359.4 kg/m$^3$) to about 6 lb/gal (718.8 kg/m$^3$), a point ranging from about 6 lb/gal (718.8 kg/m$^3$) to about 9 lb/gal (1078.2 kg/m$^3$), a point ranging from about 9 lb/gal (1078.2 kg/m$^3$) to about 12 lb/gal (1437.6 kg/m$^3$), a point ranging from about 12 lb/gal (1437.6 kg/m$^3$) to about 14 lb/gal (1677.2 kg/m$^3$), or alternatively, any range therebetween.

Friction reducing polymers may be included in the hydraulic fracturing fluid without a gelling agent to form a slickwater fluid or with a gelling agent to form a gelled fluid. The friction reducing polymer may be a synthetic polymer such as an anionic polymer, a cationic polymer, or a zwitterionic polymer. By way of example, suitable synthetic polymers may include any of a variety of monomeric units, including acrylamide, acrylic acid, 2-acrylamido-2-methyl-propane sulfonic acid, N,N-dimethylacrylamide, vinyl sulfonic acid, N-vinyl acetamide, N-vinyl formamide, itaconic acid, methacrylic acid, acrylic acid esters, methacrylic acid esters and combinations thereof. Suitable friction reducing polymers may be in an acid form or in a salt form. As will be appreciated by one of ordinary skill in the art, a variety of salts may be prepared, for example, by neutralizing the acid form of the acrylic acid monomer or the 2-acrylamido-2-methylpropane sulfonic acid monomer. In addition, the acid form of the polymer may be neutralized by ions present in the fracturing fluid.

In some embodiments, the friction reducing polymers may be viscosifying friction reducing polymers which may include any of the friction reducing polymer described above. As one of ordinary skill in the art will understand, friction reducing polymers may increase the viscosity of a fluid that they are added to. However, the increase in viscosity may be relatively low compared to the viscosity increase associated with gelling agents and viscosifying friction reducing polymers. Oftentimes it may not be economical to add enough friction reducing polymer to a fracturing fluid to increase the viscosity by an appreciable amount as compared to other chemical additives that increase fluid viscosity at a lower cost. Viscosifying friction reducing polymers may provide friction reducing properties as well as viscosifying properties. Viscosifying friction reducing polymer may be engineered to provide more viscosifying property than an equivalent amount of friction reducing polymer that is not classified as a viscosifying friction reducing polymer. The viscosifying friction reducing polymer may be provided as a water-in-oil emulsion that is inverted upon addition to the aqueous base fluid to provide viscosity and friction reduction.

As one of ordinary skill in the art will appreciate, the particular chemical composition of the viscosifying friction reducing polymers may affect the viscosifying and friction reducing properties. As discussed above, the friction reducing polymers may be synthesized to remain operable within certain ranges of total dissolved solids (TDS) while maintaining friction reducing properties. TDS may be only one of many factors that may affect the viscosifying and/or friction reducing properties of a viscosifying friction reducing polymer. Other factors may include without limitation temperature of the aqueous base fluid and oxidation-reduction potential of the aqueous base fluid.

The friction reducing polymer or viscosifying friction reducing polymer may be included in the hydraulic fracturing fluid in the form of a liquid additive, for example, an amount ranging from about 0.1 gallons of the friction reducing polymer per thousand gallons of the fracturing fluid ("GPT") to about 4 GPT. Alternatively, an amount ranging from about 0.1 GPT to about 0.5 GPT, an amount ranging from about 0.5 OPT to about 0.7 GPT, an amount ranging from about 0.7 GPT to about 1 GPT, an amount ranging from about 1 GPT to about 1.3 GPT, an amount ranging from about 1.3 GPT to about 1.6 GPT, an amount ranging from about 1.6 GPT to about 2 GPT, an amount ranging from about 2 GPT to about 2.5 GPT, an amount ranging from about 2.5 GPT to about 3 GPT, an amount ranging from about 3 GPT to about 3.5 GPT, an amount ranging from about 3.5 GPT to about 4 GPT, or alternatively, an amount ranging between any of the previously recited ranges. When provided as a liquid additive, the friction reducing polymer or viscosifying friction reducing polymer may be in the form of an emulsion, a liquid concentrate, or both. One of ordinary skill will understand that a volume ratio such as GPT is equivalent to a volume ratio using a different basis such as liters or cubic meters. Additionally, the friction reducing polymer or viscosifying friction reducing polymer may be provided as a dry additive and may be present in an amount ranging from about 0.01% wt. % to about 0.5 wt. % based on a total weight of the hydraulic fracturing fluid. Alternatively an amount ranging from about 0.01 wt. % to about 0.025 wt. %, an amount ranging from about 0.025 wt. % to about to about 0.04 wt. %, an amount ranging from about 0.04 wt. % to about 0.06 wt. %, an amount ranging from about 0.06 wt. % to about 0.09 wt. %, an amount ranging from about 0.09 wt. % to about 0.12 wt. %, an amount ranging from about 0.12 wt. % to about 0.15 wt. %, an amount ranging from about 0.15 wt. % to about 0.2 wt. %, an amount ranging from about 0.2 wt. % to about 0.25 wt. %, an amount ranging from about 0.25 wt. % to about 0.3 wt. %, an amount ranging from about 0.3 wt. % to about 0.35 wt. %, an amount ranging from about 0.35 wt. % to about 0.4 wt. %, an amount ranging from about 0.45 wt. % to about 0.5 wt. %, or alternatively, an amount ranging between any of the previously recited ranges.

Gelling agents may be included in the hydraulic fracturing fluid to increase the hydraulic fracturing fluid's viscosity which may be desired for some types of subterranean applications. For example, an increase in viscosity may be used for transferring hydraulic pressure to divert treatment fluids to another part of a formation or for preventing undesired leak-off of fluids into a formation from the buildup of filter cakes. The increased viscosity of the gelled or gelled and cross-linked treatment fluid, among other things, may reduce fluid loss and may allow the fracturing fluid to transport larger quantities of suspended proppant as compared to a non-gelled or slickwater fluid. Gelling agents may include, but are not limited to, any suitable hydratable polymer, including, but not limited to, galactomannan gums, cellulose derivatives, combinations thereof, derivatives thereof, and the like. Galactomannan gums are generally characterized as having a linear mannan backbone with various amounts of galactose units attached thereto. Examples of suitable galactomannan gums include, but are not limited to, gum arabic, gum ghatti, gum karaya, tamarind gum, tragacanth gum, guar gum, locust bean gum, combinations thereof, derivatives thereof, and the like. Other suitable gums include, but are not limited to, hydroxyethylguar, hydroxypropylguar, carboxymethylguar, carboxymethylhydroxyethylguar and carboxymethylhydroxypropylguar. Examples of suitable cellulose derivatives include hydroxyethyl cellulose, carboxyethylcellulose, carboxymethylcellulose, and carboxymethylhydroxyethylcellulose; derivatives thereof, and combinations thereof. The cross-linkable polymers included in the treatment fluids of the present disclosure may be naturally-occurring, synthetic, or a combination thereof. The crosslinkable polymers may include hydratable polymers that contain one or more functional groups such as hydroxyl, cis-hydroxyl, carboxyl, sulfate, sulfonate, phosphate, phosphonate, amino, or amide groups. In certain systems and/or methods, the crosslinkable polymers may be at least partially crosslinked, wherein at least a portion of the molecules of the crosslinkable polymers are crosslinked by a reaction including a crosslinking agent. The gelling agent may be present in the fracturing fluid in an amount ranging from about 5 lbs/1,000 gal of hydraulic fracturing fluid (0.5991 kg/m^3) to about 20 lbs/1,000 gal (2.3946 kg/m^3). Alternatively, in an amount ranging from about 5 lbs/1,000 gal (0.5991 kg/m^3) to about 10 lbs/1,000 gal (1.198 kg/m^3), in an amount ranging from about 10 lbs/1,000 gal (1.198 kg/m^3) to about 15 lb/1,000 gal (1.797 kg/m^3), in an amount ranging from about 15 lb/1,000 gal (1.797 kg/m^3) to about 20 lb/1,000 gal (2.3946 kg/m^3), or alternatively, an amount ranging between any of the previously recited ranges.

The hydraulic fracturing fluid may include any number of additional optional additives, including, but not limited to, salts, acids, fluid loss control additives, gas, foamers, corrosion inhibitors, scale inhibitors, catalysts, clay control agents, biocides, friction reducing polymers, iron control agent, antifoam agents, bridging agents, dispersants, hydrogen sulfide ("$H_2S$") scavengers, carbon dioxide ("$CO_2$") scavengers, oxygen scavengers, lubricants, viscosifiers, breakers, weighting agents, inert solids, emulsifiers, emulsion thinner, emulsion thickener, surfactants, lost circulation additives, pH control additive, buffers, crosslinkers, stabilizers, chelating agents, mutual solvent, oxidizers, reducers, consolidating agent, complexing agent, particulate materials and any combination thereof. With the benefit of this disclosure, one of ordinary skill in the art should be able to recognize and select a suitable optional additive for use in the fracturing fluid.

Figure 1:
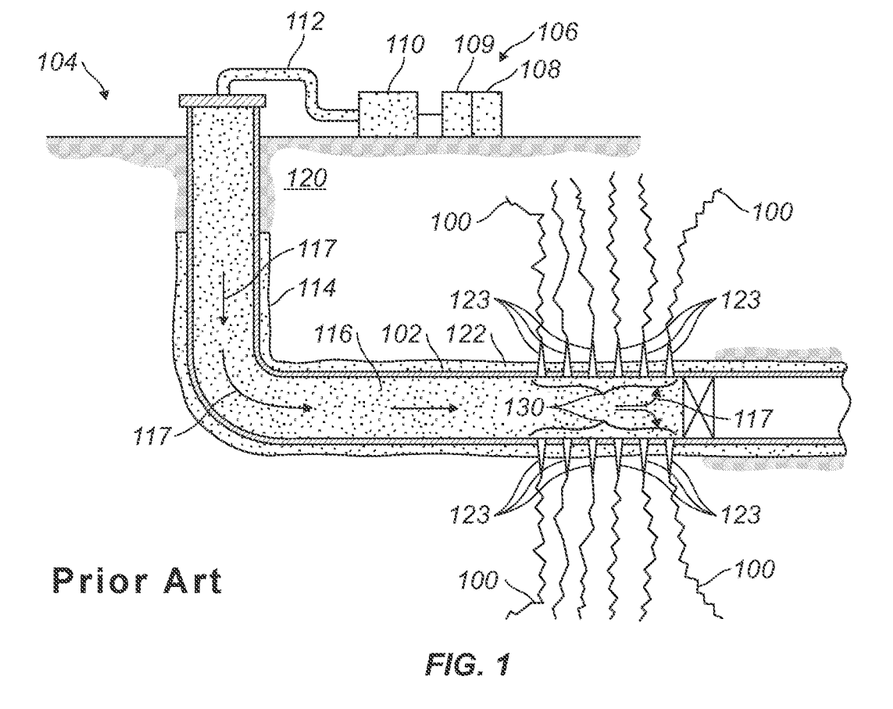
FIG. 1 is a schematic view of an example well system utilized for hydraulic fracturing.

FIG. 1 illustrates an example of a well system 104 that may be used to introduce proppant 116 into fractures 100. Well system 104 may include a fluid handling system 106, which may include fluid supply 108, mixing equipment 109, pumping equipment 110, and wellbore supply conduit 112. Pumping equipment 110 may be fluidly coupled with the fluid supply 108 and wellbore supply conduit 112 to communicate a fracturing fluid 117, which may include proppant 116 into wellbore 114. Proppant 116 may be any of the proppants described herein. The fluid supply 108 and pumping equipment 110 may be above the surface 118 while the wellbore 114 is below the surface 118.

Well system 104 may also be used for the pumping of a pad or pre-pad fluid into the subterranean formation at a pumping rate and pressure at or above the fracture gradient of the subterranean formation to create and maintain at least one fracture 100 in subterranean formation 120. The pad or pre-pad fluid may be substantially free of solid particles such as proppant, for example, less than 1 wt. % by weight of the pad or pre-pad fluid. Well system 104 may then pump the fracturing fluid 117 into subterranean formation 120 surrounding the wellbore 114. Generally, a wellbore 114 may include horizontal, vertical, slanted, curved, and other types of wellbore geometries and orientations, and the proppant 116 may generally be applied to subterranean formation 120 surrounding any portion of wellbore 114, including fractures 100. The wellbore 114 may include the casing 102 that may be cemented (or otherwise secured) to the wall of the wellbore 114 by cement sheath 122. Perforations 123 may allow communication between the wellbore 114 and the subterranean formation 120. As illustrated, perforations 123 may penetrate casing 102 and cement sheath 122 allowing communication between interior of casing 102 and fractures 100. A plug 124, which may be any type of plug for oilfield applications (e.g., bridge plug), may be disposed in wellbore 114 below the perforations 123.

In accordance with systems and/or methods of the present disclosure, a perforated interval of interest 130 (depth interval of wellbore 114 including perforations 123) may be isolated with plug 124. A pad or pre-pad fluid may be pumped into the subterranean formation 120 at a pumping rate and pressure at or above the fracture gradient to create and maintain at least one fracture 100 in subterranean formation 120. Then, proppant 116 may be mixed with an aqueous based fluid via mixing equipment 109, thereby forming a fracturing fluid 117, and then may be pumped via pumping equipment 110 from fluid supply 108 down the interior of casing 102 and into subterranean formation 120 at or above a fracture gradient of the subterranean formation 120. Pumping the fracturing fluid 117 at or above the fracture gradient of the subterranean formation 120 may create (or enhance) at least one fracture (e.g., fractures 100) extending from the perforations 123 into the subterranean formation 120. Alternatively, the fracturing fluid 117 may be pumped down production tubing, coiled tubing, or a combination of coiled tubing and annulus between the coiled tubing and the casing 102.

At least a portion of the fracturing fluid 117 may enter the fractures 100 of subterranean formation 120 surrounding wellbore 114 by way of perforations 123. Perforations 123 may extend from the interior of casing 102, through cement sheath 122, and into subterranean formation 120.

Figure 2:
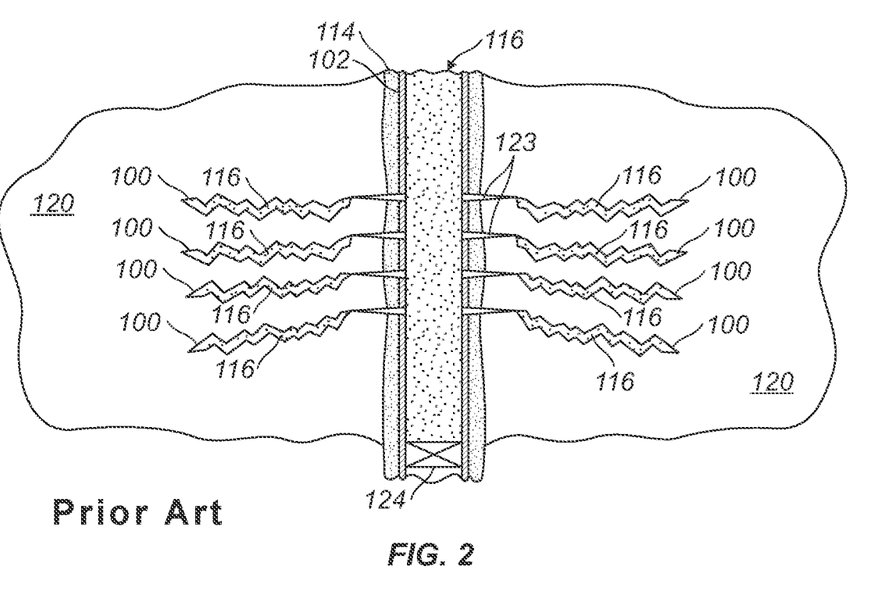
FIG. 2 is a schematic view of an example of a wellbore after introduction of fracturing fluid.

Referring to FIG. 2, the wellbore 114 is shown after placement of the proppant 116 in accordance with systems and/or methods of the present disclosure. Proppant 116 may be positioned within fractures 100, thereby propping open fractures 100.

The pumping equipment 110 may include a high pressure pump. As used herein, the term "high pressure pump" refers to a pump that is capable of delivering the fracturing fluid 117 and/or pad/pre-pad fluid downhole at a pressure of about 1000 psi (6894 kPa) or greater. A high pressure pump may be used when it is desired to introduce the fracturing fluid 117 and/or pad/pre-pad fluid into subterranean formation 120 at or above a fracture gradient of the subterranean formation 120, but it may also be used in cases where fracturing is not desired. Additionally, the high pressure pump may be capable of fluidly conveying particulate matter, such as the proppant 116, into the subterranean formation 120. Suitable high pressure pumps may include, but are not limited to, floating piston pumps and positive displacement pumps. Without limitation, the initial pumping rates of the pad fluid, pre-pad fluid and/or fracturing fluid 117 may range from about 15 barrels per minute ("bbl/min") (2385 l/min) to about 80 bbl/min (12719 l/min), enough to effectively create a fracture into the formation and place the proppant 116 into at least one fracture 101.

Alternatively, the pumping equipment 110 may include a low pressure pump. As used herein, the term "low pressure pump" refers to a pump that operates at a pressure of about 1000 psi (6894 kPa) or less. A low pressure pump may be fluidly coupled to a high pressure pump that may be fluidly coupled to a tubular (e.g., wellbore supply conduit 112). The low pressure pump may be configured to convey the fracturing fluid 117 and/or pad/pre-pad fluid to the high pressure pump. The low pressure pump may "step up" the pressure of the fracturing fluid 117 and/or pad/pre-pad fluid before it reaches the high pressure pump.

Mixing equipment 109 may include a mixing tank that is upstream of the pumping equipment 110 and in which the fracturing fluid 117 may be formulated. The pumping equipment 110 (e.g., a low pressure pump, a high pressure pump, or a combination thereof) may convey fracturing fluid 117 from the mixing equipment 109 or other source of the fracturing fluid 117 to the casing 102. Alternatively, the fracturing fluid 117 may be formulated offsite and transported to a worksite, in which case the fracturing fluid 117 may be introduced to the casing 102 via the pumping equipment 110 directly from its shipping container (e.g., a truck, a railcar, a barge, or the like) or from a transport pipeline. In either case, the fracturing fluid 117 may be drawn into the pumping equipment 110, elevated to an appropriate pressure, and then introduced into the casing 102 for delivery downhole.

A hydraulic fracturing operation may operate in stages where a bridge plug, frac plug, or other obstruction is inserted into the wellbore to prevent fluid communication with a region of the wellbore after the bridge plug. A perforating gun including explosive shaped charges may be inserted into a region of the wellbore before the bridge plug (i.e. a region where the measured depth is less than the measured depth of the bridge plug) and perforate holes through the walls of the wellbore. The perforating gun may be removed from the wellbore and a fracturing fluid introduced thereafter. The stage is completed when the planned volume of fluid and proppant has been introduced into the subterranean formation. Another stage may begin with the insertion of a second bridge plug into a wellbore region before the bridge plug.

As previously mentioned, a total dissolved solids concentration may vary between fracturing stages or vary within a stage. The performance of a friction reducing polymer in a hydraulic fracturing fluid may be adversely affected by the total dissolved solids content of the aqueous base fluid used to make the hydraulic fracturing fluid. In particular, multi-valent cations such as calcium, iron, magnesium, and single valent cations such as sodium and potassium may prevent friction reducing polymer from fully hydrating and prevent the friction reducing polymer from performing well in the hydraulic fracturing fluid. There may exist friction reducing polymers that are able to overcome the adverse effects of single valent and multivalent, however, such friction reducing polymers may be costly. A total dissolved solids (TDS) measurement may provide an estimate of the concentration of single valent and multivalent in the aqueous base fluid which may allow a user to select a friction reducing polymer that will perform at a particular TDS level.

Figure 3:
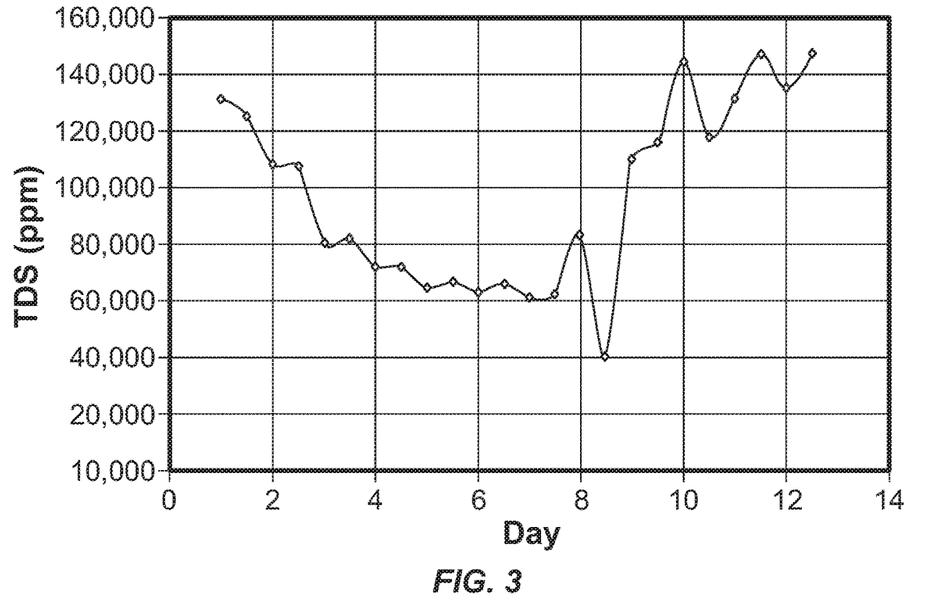
FIG. 3 illustrates a graph of total dissolved solids over time for a water source.

FIG. 3 illustrates an example of a water source wherein the TDS concentration over a period of 12 days was monitored. The TDS concentration was found to vary between about 150,000 parts per million (ppm) at a high and 40,000 ppm at a low. As one of ordinary skill in the art will appreciate, a hydraulic fracturing operation may require multiple days or weeks to complete depending on the number of stages a particular well will require and the number of wells on a particular pad site being fractured. If a single laboratory test was performed to determine the TDS and a hydraulic fracturing fluid was prepared with a selected friction reducing polymer based on the measured TDS, the friction reducing polymer may not perform satisfactory over the entire time period of fracturing.

Some friction reducing polymer may be available for different TDS levels, for example, <20 k TDS, 0-70 k TDS, 0-120 k TDS, 40-200 k TDS, and 150-350 k TDS. Measurements of TDS may have units of parts per million (ppm), for example. 1 ppm is equivalent to 1 milligram of dissolved solids per kilogram of water. However, there may be few friction reducing polymer available that are economical that will cover the entire range of TDS such as from 0-200 k TDS. Furthermore, each specific friction reducing polymer has a particular operating band where the friction reducing polymer performs best. In general, friction reducing polymers that are designed to operate in relatively higher TDS environments are more expensive per unit volume than a friction reducing polymer that is designed to operate in a relatively lower TDS environment. When the TDS level approaches the upper limit for a particular friction reducing polymer, a concentration of the particular friction reducing polymer may need to be increased to compensate for the loss of friction reduction ability. The increased concentration of friction reducing polymer may cause an increase in operating costs and have other adverse effects on other chemical species of the hydraulic fracturing fluid. Similarly, if a TDS level drops below an operating range where the friction reducing polymer is designed to operate, there may be additional operational costs to using the relatively more expensive friction reducing polymer when a relatively cheaper friction reducing polymer is available that would perform adequately at the lower TDS level.

One important factor in selecting the type of friction reducing polymer may be the pressure response at the wellhead. A pressure transducer may be coupled to the wellhead, headers, risers, or other equipment fluidically coupled to the wellbore that may allow a pressure at the surface to be monitored. If a friction reducing polymer becomes ineffective due to a TDS level of the water source changing, a resultant pressure increase may be observed at the pressure transducer due to the friction reducing polymer being unable to reduce fluid friction at a higher TDS concentration. The wellhead pressure response may provide a measurement of the effectiveness of the friction reducing polymer at reducing friction in a conduit. Performance of a friction reducing polymer may also be monitored in a flow loop where a fluid including the friction reducing polymer is circulated continuously in a loop, passing through a measurement section. Pressure response of the fluid may be measured in the measurement section as the composition of the fluid is varied. A flow loop may provide a method to test friction reducing polymers while varying TDS concentration. The example section of the present disclosure illustrates some results of testing various friction reducing polymers in a flow loop.

Laboratory testing may be performed on friction reducing polymers to determine the operational limits of each friction reducing polymer. A fluid including a friction reducing polymer may be subjected to a pressure response test in a flow loop, for example, or other suitable laboratory methods to determine a percent reduction in pressure loss while varying one or more concentrations of ions in the fluid. The specific ion of interest, such as calcium for example, may be varied from zero up to a point where the friction reducing polymer has reduced performance. Reduction in performance may be observed as a decrease in pressure reduced (i.e. the pressure increases) over a period of time. For example, a particular friction reducing polymer may reduce pressure by 70% with zero cation concentration but at 40,000 PPM calcium, may only reduce pressure by 40% and then decrease to zero percent reduction over a period of time. The friction reducing polymer may be tested with other ions such as iron to generate a complete operational limit of the friction reducing polymer. The data relating to the operational limits of each friction reducing polymer may be stored in an operational database, for example. In some examples, the operational database may be a historical database as will be described in detail below.

A method is described that allows for one of ordinary skill in the art to dynamically select an appropriate friction reducing polymer for a particular TDS level to reduce operational costs associated with hydraulic fracturing operations. The methods described herein may generally couple laboratory testing techniques to obtain real-time water quality analyses with archival data on both water analyses across historical fracturing jobs and laboratory testing data of friction reducing polymers. The laboratory testing techniques may determine one or more properties that may be correlated to determine TDS concentration. Some laboratory testing techniques may include, but are not limited to, conductivity measurement, density measurement, pH measurement, temperature measurement, viscosity measurement, flow loop measurement, and combinations thereof. The laboratory testing techniques do not necessarily have to be performed in a laboratory. The testing techniques may also be performed any time before the fracturing fluid is made. For example, the testing techniques may be performed in line with a water source used for making the hydraulic fracturing fluid. The testing may be performed by positioning testing equipment such as a conductivity probe, a densometer, temperature probe, viscosity probe, flow loop or combination thereof before a blender tub where the fracturing fluid is blended. The testing equipment may be placed, without limitation, on a fluid header, a fluid tank, in line with a hose, in an inlet to a blender tub, or in any position before the blender tub. Spectrographic techniques may also be used to determine ion concentrations.

Conductivity measurements may be made using a conductivity probe or multi meter. The conductivity probe may be of any type, for example, potentiometric type or inductive type. As one of ordinary skill in the art will appreciate, dissolved ionized solids such as salts and minerals increase the electrical conductivity measurement of a solution. Measuring conductivity may yield an indirect measurement of TDS. As previously discussed, the TDS measurement may be correlated to an ion concentration using a historical database. For a particular water source, the historical database may include data points for conductivity and individual ion concentrations such that a correlation of conductivity versus ion concentration may be calculated. The correlation may be used to determine a total ion concentration as well as concentrations of individual ion species from a conductivity measurement.

Density measurements may be made using any kind of densometer. For example, gravitic density meters, Coriolis density meters, nuclear density meters, microwave density meters, ultrasonic density meters, or any combination thereof. Alternatively, density may be calculated using refractive index measurements. As one of ordinary skill in the art will appreciate, a density of a solution will increase with increasing concentration of dissolved solids. Measuring density of a solution may yield an indirect measurement of TDS which may then be correlated to an ion concentration using a historical database. For a particular water source, the historical database may include data points for density and individual ion concentrations such that a correlation of conductivity versus ion concentration may be calculated. The correlation may be used to determine a total ion concentration as well as concentrations of individual ion species from a density measurement.

Figure 4:
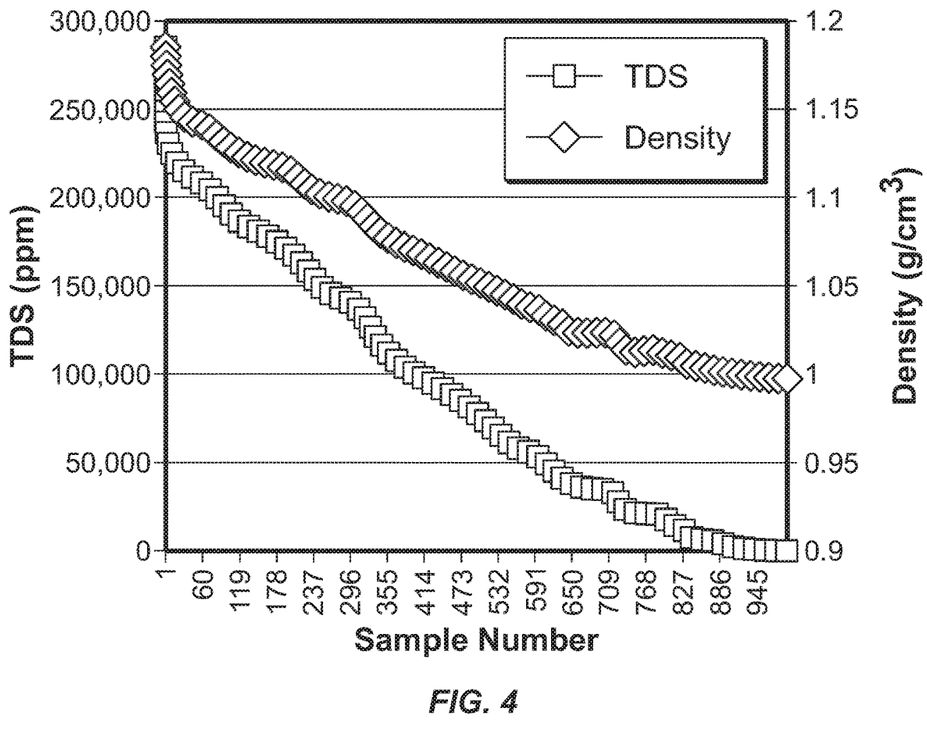
FIG. 4 illustrates a plot of total dissolved solids and of water samples taken from a particular water region.
Figure 5:
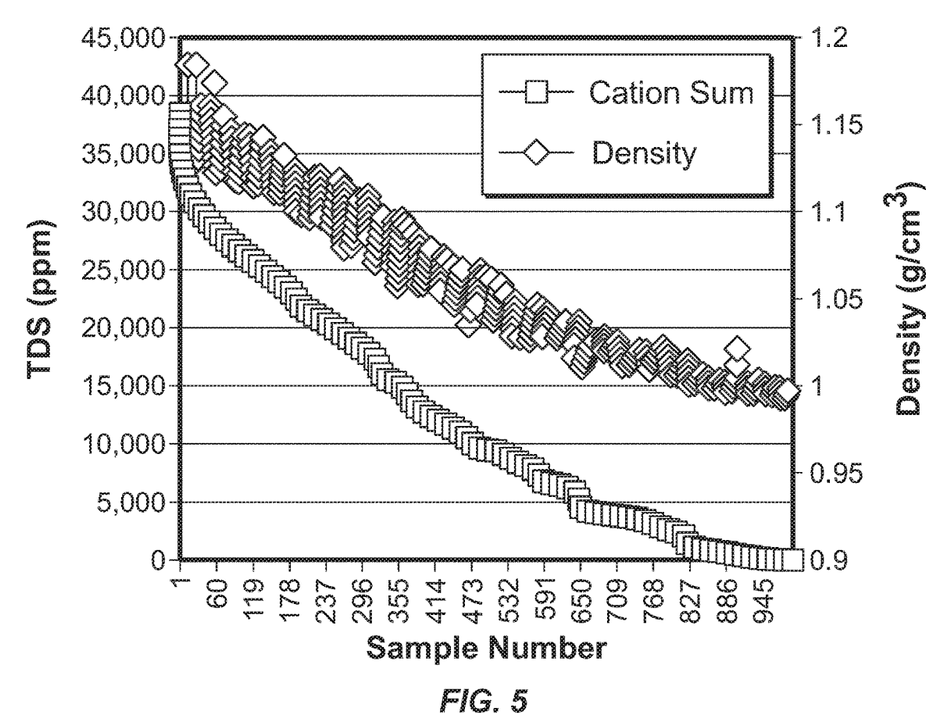
FIG. 5 illustrates a plot of total dissolved solids and of water samples taken from a particular water region.

FIG. 4 illustrates a plot of TDS and density for about 1000 water samples taken from a particular water region. It is observed that there is a strong correlation between density and TDS for the particular samples. Given the strong correlation between density and TDS, a TDS estimate may be made for a sample of water taken from the particular region by measuring the density of the sample and correlating the sampled density to the plot of FIG. 4. With reference to FIG. 5, another example of a dissolved solids and density plot is illustrated, wherein the dissolved solids is a count of the total cations in the sample. Again it is observed that there is a strong correlation between concentration of cations and density. Given the strong correlation between density and dissolved cation concentration, a dissolved cation concentration estimate may be made for a sample of water taken from the particular region by measuring the density of the sample. The plots from FIGS. 4 and 5 may be considered part of a historical database. Additionally, the data points may indicate the maximum ion concentrations observed from the particular water region over a period of time as well. For example, with reference to FIG. 5, if a particular sample has a density of about 1 $g/cm^3$, the expected cation concentration would be approximately 22,000-30,000 ppm. A friction reducing polymer that is operable up to 30,000 ppm may be selected to blend a fracturing fluid if a measured density of the water is about 1 $g/cm^3$ and the water used to blend the fracturing fluid is from the particular region used to generate the data of FIG. 5.

A historical database for a particular source of water may be constructed by monitoring the TDS concentration of a source of water and measuring density, ion levels, pH, temperature, or combinations thereof to generate data bout the source of water. A historical database may allow correlations to be made to predict the concentration of ions in a sample of water from the source of water. In particular, a density or conductivity measurement may be used to determine the TDS level which may then be correlated to calcium and iron concentration in a sample of water. The historical database may also contain the identities and concentrations of the species of ions at the particular measured TDS level.

Oftentimes a fracturing fluid has particular physical parameters that must be within a set range or specification. Some physical parameters may include viscosity and pH, for example, as these parameters may affect the performance of the fracturing fluid. Viscosity may affect the ability of the fracturing fluid to transport particulate such as proppant into a fracture. In general a lower viscosity fluid requires a higher pipe flow velocity to keep proppant suspended in the fluid than a fluid with a higher viscosity. The fracturing fluid may be designed with a particular range of acceptable viscosities that will allow adequate suspension of the proppant but also keep pump power requirements within acceptable levels. An increase in fluid viscosity may be associated with an increased horsepower requirement to pump the more viscous fluid which may increase costs and equipment. The pH of a fracturing fluid may affect hydration of gels and friction reducing polymers.

The fracturing fluid may have a requirement of a particular viscosity or range of viscosity leaving a fracturing blender. The viscosity of a hydraulic fracturing fluid prepared with a viscosifying friction reducing polymer may be a function of the initial viscosity of the aqueous base fluid and the viscosity contribution of the viscosifying friction reducing polymer and other viscosity increasing additives. A method to prepare a fracturing fluid with a particular viscosity may include using a viscosity probe to determine viscosity of a water source before the water enters a blender tub. The viscosity probe may be placed, without limitation, on a fluid header, a fluid tank, in line with a hose, in an inlet to a blender tub, or in any position before the blender tub. The method may further include measuring at least one of the temperature, density, and TDS levels of the water source entering the blender tub. As discussed above, the chosen friction reducer or viscosifying friction reducer may have a temperature dependent viscosity contribution. For different temperature water, the viscosifying friction reducer may provide relatively more or relatively less viscosity to a hydraulic fracturing fluid at the same viscosifying friction reducer concentration. To more accurately predict the viscosity of the fracturing fluid leaving the blender tub, temperature dependent viscosity effects of viscosity may be considered when determining the concentration of viscosifying friction reducing polymer to include in a particular fracturing fluid.

A workflow for selecting a viscosifying friction reducing polymer and concentration thereof may include measuring viscosity of a water source, measuring density of the water source, and measuring or calculating TDS concentration and/or chemical identity of the dissolved species in the water source using a historical database for the particular source of water. A viscosifying friction reducing polymer may be selected based on the TDS concentration and/or chemical identity of the dissolved species. The required concentration of the viscosifying friction reducing polymer to achieve a particular viscosity may be calculated from at least one of the measured temperature, measured viscosity, or an operational database of including operational limits of viscosifying friction reducing polymers.

Figure 10:
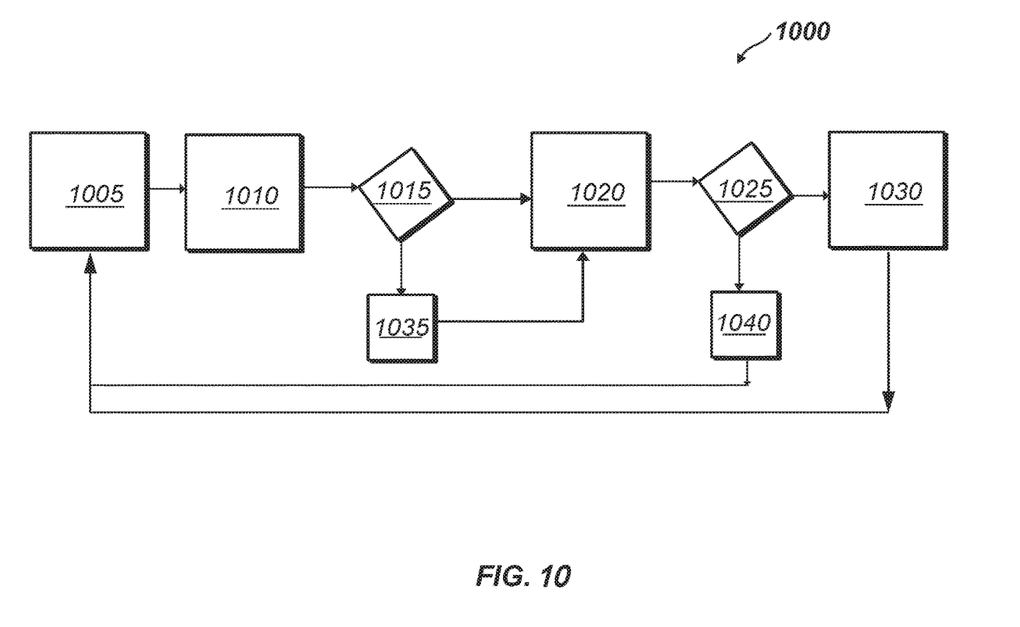
FIG. 10 illustrates a methodology of selecting a friction reducing polymer.

FIG. 10 illustrates a workflow 1000 for selecting a viscosifying friction reducing polymer and concentration thereof. Workflow 1000 may begin at block 1005 whereby fluid characteristics such as TDS, viscosity, pH, turbidity, density, and other characteristics are measured. The measurement gathered in block 1005 may be checked against a historical database in block 1010. In decision block 1015, the dosage checkpoint for the friction reducing polymer is checked against the required dosage set point as dictated by the historical database in block 1010. If the set point is at the correct level, the method may proceed to block 1020 whereby friction reducer flow may be stated. Alternatively, if the set point is not at the correct level, the method may proceed to block 1035 whereby the set point may be adjusted and thereafter the method may proceed to block 1020. In decision block 1025, the fluid response such as pressure and viscosity is compared to the set point fluid response. If the fluid response is at the correct set point fluid response, the method may proceed to block 1030 whereby the friction reducer flow may be maintained. If the fluid response is not at the correct set point fluid response, the method may proceed to block 1040 whereby the operational conditions such as fluid characteristics, set point, and set point fluid response may be recorded and save into the operational database.

A method may include using a conductivity probe to determine the TDS level of a water source before entering a blender unit for blending a hydraulic fracturing fluid. As previously discussed, the conductivity probe may be placed anywhere before the water enters the blender tub for example. The TDS level may then be correlated using the historical database to a highest concentration of calcium and iron at the TDS level. An operational database including operational limits of friction reducing polymers may be referenced to determine which friction reducing polymers that will perform adequately at the highest concentration of calcium and iron. A friction reducing polymer may then be selected based at least in part on the determination of which friction reducing polymers will perform adequately. The selected friction reducing polymer may then be used in the blending of the hydraulic fracturing fluid.

A method may include using a densometer to determine the density of a water source before entering a blender unit for blending a hydraulic fracturing fluid. As previously discussed, the densometer may be placed anywhere before the water enters the blender tub for example. The density may then be correlated using the historical database to a highest concentration of calcium and iron at the density level. An operational database including operational limits of friction reducing polymers may be referenced to determine which friction reducing polymers that will perform adequately at the highest concentration of calcium and iron. A friction reducing polymer may then be selected based at least in part on the determination of which friction reducing polymers will perform adequately. The selected friction reducing polymer may then be used in the blending of the hydraulic fracturing fluid.

A method may include using a flow loop to determine a friction reducing polymer performance with a water source before entering a blender unit for blending a hydraulic fracturing fluid. The TDS level may be determined by any of the previously mentioned methods. The historical database and operational database may then be referenced to determine friction reducing polymer performance for various friction reducing polymer produces at the TDS level measured. A friction reducing polymer may then be selected based at least in part on the determination of which friction reducing polymers will perform adequately. The selected friction reducing polymer may then be used in the blending of the hydraulic fracturing fluid.

A method may include using a conductivity probe to determine the TDS level of a water source before entering a blender unit for blending a hydraulic fracturing fluid. As previously discussed, the conductivity probe may be placed anywhere before the water enters the blender tub for example. The TDS level may then be correlated using the historical database to a highest concentration of calcium and iron at the TDS level. An operational database including operational limits of friction reducing polymers may be referenced to determine which friction reducing polymers that will perform adequately at the highest concentration of calcium and iron. A friction reducing polymer may then be selected based at least in part on the determination of which friction reducing polymers will perform adequately. The selected friction reducing polymer may then be used blended to a fracturing fluid and tested in a flow loop for performance. If the performance of the friction reducing polymer is adequate the friction reducing polymer may be used to blend a hydraulic fracturing fluid.

A method may include using a densometer to determine the density of a water source before entering a blender unit for blending a hydraulic fracturing fluid. As previously discussed, the densometer may be placed anywhere before the water enters the blender tub for example. The density may then be correlated using the historical database to a highest concentration of calcium and iron at the density level. An operational database including operational limits of friction reducing polymers may be referenced to determine which friction reducing polymers that will perform adequately at the highest concentration of calcium and iron. A friction reducing polymer may then be selected based at least in part on the determination of which friction reducing polymers will perform adequately. The selected friction reducing polymer may then be used blended to a fracturing fluid and tested in a flow loop for performance. If the performance of the friction reducing polymer is adequate the friction reducing polymer may be used to blend a hydraulic fracturing fluid.

A method may include using a densometer to determine the density or conductivity meter to determine conductivity. As previously discussed, density and conductivity may be correlated to TDS levels. Equilibrium equations may then be used to determine calcium and iron levels for TDS at different densities and conductivities. An operational database including operational limits of friction reducing polymers may be referenced to determine which friction reducing polymers that will perform adequately at the calculated concentration of calcium and iron. A friction reducing polymer may then be selected based at least in part on the determination of which friction reducing polymers will perform adequately. As used herein, perform adequately means that in a laboratory test, such as a flow loop test, the friction reducing polymer will not lose more than 15% friction reduction ability for a period of 15 minutes. The selected friction reducing polymer may then be used to blend a fracturing fluid which may then be tested in a flow loop for performance. If the performance of the friction reducing polymer is adequate the friction reducing polymer may be used to blend a hydraulic fracturing fluid for pumping into a subterranean formation.

Figure 9:
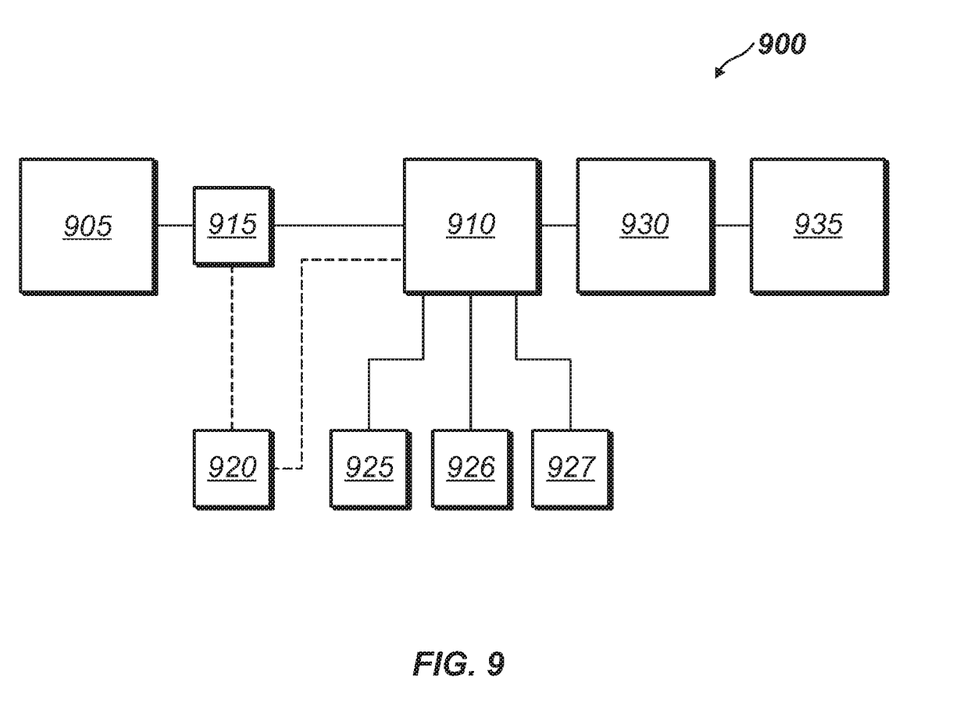
FIG. 9 illustrates a schematic of a hydraulic fracturing system.

FIG. 9 illustrates a system 900 using the methods described herein. A source of water 905 may be fluidically coupled to a hydraulic fracturing blender 910. Source of water 905 may be any source of water described herein including, but not limited to, a tank, a water header, a water well, or a surface body of water such as a lake, stream, pond, and ocean, or the like. Hydraulic fracturing blender 910 may include all equipment required to prepare a hydraulic fracturing fluid, including, but not limited to, a blender tub, proppant addition equipment such as sand screws, centrifugal pumps, liquid additive pumps, and other equipment well known in the art. Water testing equipment 915 may be placed in line between source of water 905 and hydraulic fracturing blender 910. Water testing equipment 915 may be any of the equipment previously mentioned including a densometer, a conductivity meter, a spectrometer, a flow loop, a viscosity probe, or any combinations thereof. Water testing equipment 915 may be electrically coupled to control system 920 which may be operable to control hydraulic fracturing blender 910. Water testing equipment 915 may send an output signal to control system 920 which may provide information about density, conductivity, spectrographic output, or flow characteristics such as pressure response to control system 920.

Control system 920 may include a computer system capable of interacting with and controlling valves, motors, pumps, and other equipment in hydraulic fracturing blender 910. The computer system may include software capable of controlling equipment in hydraulic fracturing blender 910 in the form of a computer program on a non-transitory computer readable media, such as a CD, a DVD, a USB drive, a portable hard drive, ROM, RAM, or other portable memory. A processor may read the software from the computer readable media through an input/output device and store the software in memory where it is prepared for execution through compiling and linking, if necessary, and then executed. In one example, control system 920 may accepts input through an input/output device such as a keyboard or keypad, mouse, touchpad, touch screen, etc., and provides outputs through an input/output device such as a monitor or printer. Control system 920 may also accept inputs and send outputs to and from hydraulic fracturing blender 910 and water testing equipment 915.

The software of control system 920 may include a historical database and operational database as previously described. In some examples the historical database and operational database may the same database. Control system 920 may receive an input signal from water testing equipment 915 which the software may then use to correlate to a TDS concentration using, for example, a calibration curve. The software may further correlate the TDS to an ion concentration using the historical database as previously discussed. The software may reference the operational database to determine which friction reducing polymers perform adequately at the ion concentration and select a friction reducing polymer to blend with a hydraulic fracturing fluid.

FIG. 9 illustrates a first friction reducing polymer source 925, a second friction reducing source 926, and a third friction reducing source 927. Each friction reducing polymer source may be provided as a tank, chemical tote, chemical barrel, dry additive, or by any other means. Each friction reducing polymer source may be fluidically coupled or otherwise operable to be added to the blender tub of hydraulic fracturing blender 910. The friction reducing polymer source may be fluidically coupled to the blender tub by a liquid additive pump for example. Although only three friction reducing polymer sources are illustrated in FIG. 9, any number of friction reducing polymer sources may be used. Control system 920 may determine an ion concentration as previously described and select a friction reducing polymer from first friction reducing polymer source 925, second friction reducing source 926, third friction reducing source 927 or a combination thereof to add to the blender tub based at least in part on the ion concentration and performance characteristics of each friction reducing polymer at the particular ion concentration. Control system 920 may use temperature measurements, viscosity measurements, TDS measurement or calculation from water testing equipment 915, and historical and/or operational databases to determine the concentrations and identity of friction reducing polymers to include in a fracturing fluid.

During a hydraulic fracturing stage, hydraulic fracturing blender 910 may blend a hydraulic fracturing fluid including the source of water 905 and friction reduction agent selected based at least in part on the ion concentration and discharge the hydraulic fracturing fluid to pump 930. Pump 930 may be a high pressure pump, for example, a pump capable of pressurizing the hydraulic fracturing fluid to about 10,000 psi or greater. Pump 930 may be capable of generating a pressure above a fracture gradient of a formation penetrated by wellbore 935. Pump 930 may pressurize the hydraulic fracturing fluid above the fracture gradient of the formation and discharge the hydraulic fracturing fluid into wellbore 935.

As previously described, a TDS concentration of the source of water 905 may vary with time such as between hydraulic fracturing stages or during a hydraulic fracturing stage and a change in TDS concentration may negatively affect a pressure response performance of a friction reducing polymer in a hydraulic fracturing fluid. The system 900 may be able to dynamically compensate for the changes in TDS concentration between or during a hydraulic fracturing stage. Water testing equipment 915 may continuously or discretely measure a property of the source of water 905 and send a signal to control system 920. Control system 920 may continually reference the historical database to determine if an ion concentration of the source of water is within the operable range of the friction reducing polymer being added to the blender tub. If the control system 920 determines that the ion concentration is outside of the operable range, the control system 920 may stop adding the friction reducing polymer that is outside the operable range and switch to another friction reducing polymer that is within the operable range. Alternatively, switching friction reducing polymers may be performed manually by an operator.

Accordingly, the present disclosure may be practiced according to one or more of the following statements.

Statement 1. A method comprising: providing a fracturing fluid viscosity; measuring at least one of a conductivity or a density of a water source and measuring at least one of a temperature or a viscosity of the water source; correlating at least one of the conductivity or the density of a water source to a total dissolved solids (TDS) concentration; correlating the TDS concentration of the water source to an ion concentration; and selecting at least one species and concentration of friction reducing polymer based at least in part on the fracturing fluid viscosity and at least one of the ion concentration, the temperature, or the viscosity of the water source; and preparing a fracturing fluid comprising an aqueous base fluid and the at least one species and concentration of friction reducing polymer.

Statement 2. The method of claim 1 wherein the step of measuring further comprises measuring a, reflected ration, and emitted radiation, an oxidation reduction potential or a combination thereof.

Statement 3. The method of claim 1 wherein the steps of correlating comprise correlating the TDS concentration using a historical database, the historical database comprising a trend of density, conductivity or both to TDS concentration and TDS concentration to ion concentration.

Statement 4. The method of claim 1 wherein the ion concentration is a concentration of at least one Group(I) ion, at least one Group(II) ion, at least one metal ion, or a combination thereof.

Statement 5. The method of claim 1 wherein the step of selecting at least one species and concentration of friction reducing polymer comprises using a historical database and correlating the ion concentration to friction reducing polymers that reduce friction at the ion concentration.

Statement 6. The method of claim 1 wherein the step of preparing comprises adding the selected at least one friction reducing polymer to a blender tub comprising water from the water source.

Statement 7. The method of claim 1 further comprising measuring a conductivity of the water source to determine the TDS concentration, wherein the step of correlating comprises correlating the TDS concentration using a historical database, the historical database comprising a trend of TDS concentration to ion concentration, and wherein the method further comprises adding the selected at least one friction reducing polymer to a hydraulic fracturing fluid comprising water from the water source.

Statement 8. The method of claim 1 wherein the selecting at least one friction reducing polymer is automatic.

Statement 9. The method of claim 1 wherein the selecting at least one friction reducing polymer is manually done by a user.

Statement 10. A method comprising: providing a fracturing fluid viscosity; measuring at least one of a conductivity or a density of a water source and measuring at least one of a temperature or a viscosity of the water source; correlating at least one of the conductivity or the density of a water source to a total dissolved solids (TDS) concentration; correlating the TDS concentration of the water source to an ion concentration; and selecting at least one species and concentration of friction reducing polymer based at least in part on the fracturing fluid viscosity and at least one of the ion concentration, the temperature, or the viscosity of the water source; and introducing the at least one friction reducing polymer and water from the water source into a flow loop.

Statement 11. The method of claim 10 wherein the step of measuring further comprises measuring a, reflected ration, and emitted radiation, an oxidation reduction potential or a combination thereof.

Statement 12. The method of claim 10 wherein the steps of correlating comprise correlating the TDS concentration using a historical database, the historical database comprising a trend of density, conductivity or both to TDS concentration and TDS concentration to ion concentration.

Statement 13. The method of claim 10 wherein the step of selecting at least one species and concentration of friction reducing polymer comprises using a historical database and correlating the ion concentration to friction reducing polymers that reduce friction at the ion concentration.

Statement 14. The method of claim 10 further comprising comprises adding the selected at least one friction reducing polymer to a blender tub comprising water from the water source.

Statement 15. A system comprising: a source of water fluidically coupled to a fracturing blender; water testing equipment disposed between the source of water and the fracturing blender wherein the water testing equipment is operable to measure at least one property of the source of water; a plurality of friction reducing polymers operable to be added to the fracturing blender; and a control system comprising: at least one processor; and a memory coupled to the processor to provide software that configures the processor to receive an input signal from the water testing equipment, access a historical database, use the historical database to correlate the property to a concentration of at least one Group(I) ion, at least one Group(II) ion, at least one metal ion, or a combination thereof, select at least one of the plurality of friction reducing polymers based at least in part on the concentration of at least one Group(I) ion, at least one Group(II) ion, at least one metal ion, or a combination thereof, and send an output signal to the fracturing blender to add the at least one of the plurality of friction reducing polymers to the fracturing blender.

Statement 16. The system of claim 15 wherein the water testing equipment is a densometer, a conductivity meter, a temperature probe, a densometer, a flow loop, a spectroscope, or a combination thereof.

Statement 17. The system of claim 15 wherein the friction reducing polymers are provided as a liquid, a powder, or a combination thereof.

Statement 18. The system of claim 15 wherein the historical database comprises a trend of TDS concentration to ion concentration.

Statement 19. The system of claim 15 wherein the step of selecting at least one friction reducing polymer comprises using a historical database and correlating the ion concentration to friction reducing polymers that reduce friction at the ion concentration.

Statement 20. The system of claim 19 wherein the friction reducing polymer selected will not lose more than 15% friction reduction ability for a period of 15 minutes at the ion concentration.

EXAMPLES

To facilitate a better understanding of the present invention, the following examples of certain aspects of some embodiments are given. In no way should the following examples be read to limit, or define, the entire scope of the invention.

Example 1

Figure 6:
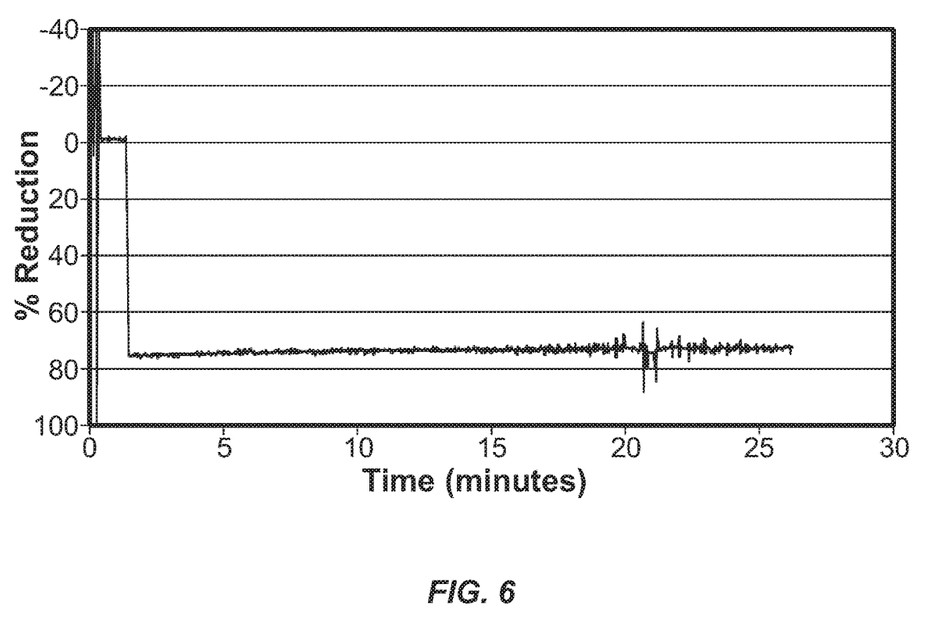
FIG. 6 illustrates results of a flow loop test for a friction reducing polymer.

A friction reducing flow loop test was performed to determine the performance of a friction reducing polymer over time. FIG. 6 illustrates the results of the experiment. The friction reducing polymer was Legend™ LD-2600 Anionic Liquid Friction Reducer available from Halliburton Energy Services at 0.5 gallons per thousand gallons (GPT)

concentration. It was observed that the friction reducing polymer was ineffective at reducing friction for about 1 minute until the friction reducing polymer was fully hydrated. It was then observed that the friction was reduced by approximately 75% for a period of about 26 minutes before the test was terminated.

Example 2

Figure 7:
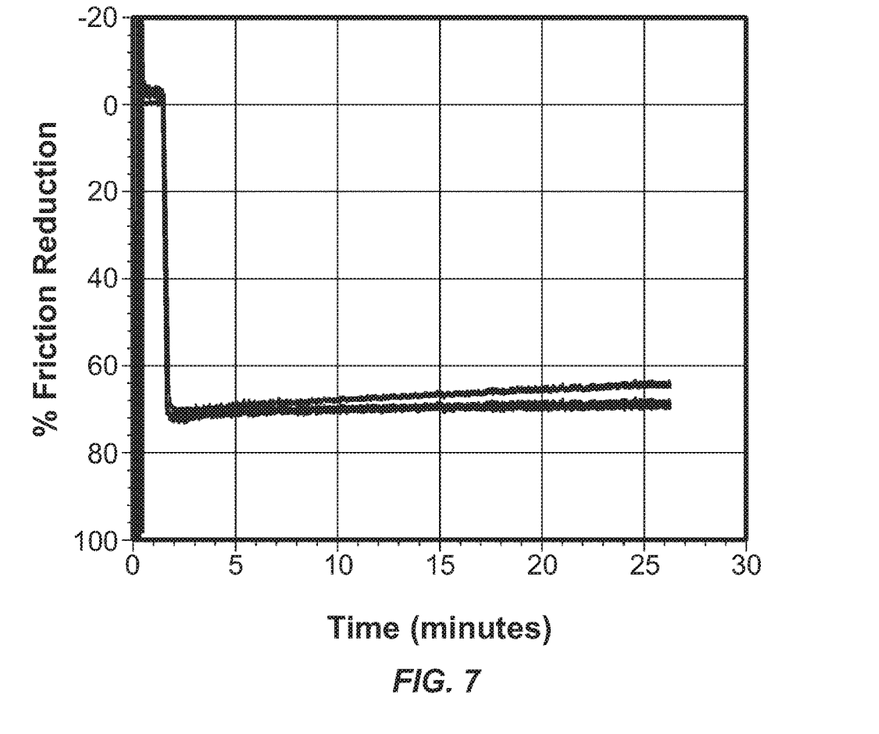
FIG. 7 illustrates results of a flow loop test for a set of friction reducing polymers.

A friction reducing flow loop test was performed on Legend™ LD-2600 Anionic Liquid Friction Reducer at 0.5, 0.75, and 1.0 GPT concentrations to determine the relative performance the friction reducing polymer concentrations over time. FIG. 7 illustrates the results of the experiment. It was observed that at each concentration, the friction reducing polymer was ineffective at reducing friction for about 1 minute until the friction reducing polymer was fully hydrated. It was then observed that the friction was reduced by approximately 70% for each concentration for a period of about 26 minutes before the test was terminated.

Example 3

Figure 8:
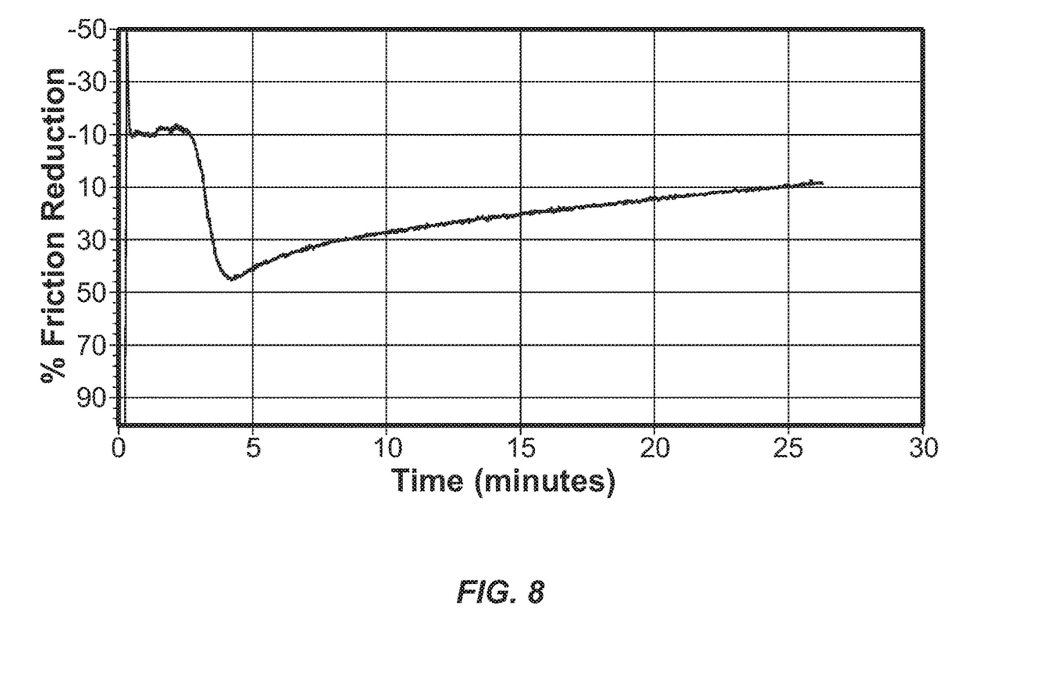
FIG. 8 illustrates results of a flow loop test for a friction reducing polymer.

A friction reducing flow loop test was performed with Legend™ LD-2600 Anionic Liquid Friction Reducer at 0 1.0 GPT concentration to determine the performance of with a TDS concentration above the friction reducing polymer's operable range. FIG. 8 illustrates the results of the experiment. It was observed that the friction reducing polymer increased the observed friction for a period of about 2.5 minutes before decreasing observed friction to approximately 49% at 4 minutes. The friction reducing polymer became less effective at reducing friction between 4 minutes until 26 minutes from reducing 49% friction to reducing 10% friction.

Therefore, the present embodiments are well adapted to attain the ends and advantages mentioned as well as those that are inherent therein. The particular embodiments disclosed above are illustrative only, as the present embodiments may be modified and practiced in different but equivalent manners apparent to those skilled in the art having the benefit of the teachings herein. Although individual embodiments are discussed, all combinations of each embodiment are contemplated and covered by the disclosure. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method comprising:
providing a fracturing fluid having a viscosity requirement measuring at least one of a conductivity or a density of a water source and measuring at least one of a temperature or a viscosity of the water source;
correlating at least one of the conductivity or the density of a water source to a total dissolved solids (TDS) concentration of the water source;
correlating the TDS concentration of the water source to an ion concentration of the water source; and
selecting at least one species and concentration of friction reducing polymer based at least in part on the fracturing fluid viscosity requirement and at least one of the ion concentration, the temperature, or the viscosity of the water source; and
preparing a fracturing fluid comprising an aqueous base fluid and the at least one species and concentration of friction reducing polymer.

2. The method of claim 1 wherein the step of measuring further comprises measuring a reflected radiation, an emitted radiation, an oxidation reduction potential or a combination thereof.

3. The method of claim 1 wherein the steps of correlating comprise correlating the TDS concentration of the water source using a historical database, the historical database comprising a trend of density, conductivity or both to TDS concentration of the water source and TDS concentration of the water source to ion concentration of the water source.

4. The method of claim 3 wherein the historical database is an operational database, wherein the operational database comprises operational limits of friction reducing polymers.

5. The method of claim 1 wherein the ion concentration of the water source is a concentration of at least one Group(I) ion, at least one Group(II) ion, at least one metal ion, or a combination thereof.

6. The method of claim 1 wherein the step of selecting at least one species and concentration of friction reducing polymer comprises using a historical database and correlating the ion concentration of the water source to friction reducing polymers that reduce friction at the measured ion concentration of the water source.

7. The method of claim 1 wherein the step of preparing comprises adding the selected at least one friction reducing polymer to a blender tub comprising water from the water source.

8. The method of claim 1 further comprising measuring a conductivity of the water source to determine the TDS concentration, wherein the step of correlating comprises correlating the TDS concentration using a historical database, the historical database comprising a trend of TDS concentration to ion concentration, and wherein the method further comprises adding the selected at least one friction reducing polymer to a hydraulic fracturing fluid comprising water from the water source.

9. The method of claim 1 wherein the selecting at least one friction reducing polymer is automatic.

10. The method of claim 1 wherein the selecting at least one friction reducing polymer is manually done by a user.

11. A method comprising:
providing a fracturing fluid having a viscosity requirement;
measuring at least one of a conductivity or a density of a water source and measuring at least one of a temperature or a viscosity of the water source;
correlating at least one of the conductivity or the density of a water source to a total dissolved solids (TDS) concentration of the water source;
correlating the TDS concentration of the water source to an ion concentration of the water source; and
selecting at least one species and concentration of friction reducing polymer based at least in part on the fracturing fluid viscosity requirement and at least one of the ion concentration, the temperature, or the viscosity of the water source; and
introducing the at least one friction reducing polymer and water from the water source into a flow loop.

12. The method of claim 11 wherein the step of measuring further comprises measuring a reflected radiation, and emitted radiation, an oxidation reduction potential or a combination thereof.

13. The method of claim 11 wherein the steps of correlating comprise correlating the TDS concentration of the water source using a historical database, the historical database comprising a trend of density, conductivity or both to TDS concentration of the water source and TDS concentration of the water source to ion concentration of the water source.

14. The method of claim 11 wherein the step of selecting at least one species and concentration of friction reducing polymer comprises using a historical database and correlating the ion concentration of the water source to friction reducing polymers that reduce friction at the measured ion concentration of the water source.

15. The method of claim 11 further comprising comprises adding the selected at least one friction reducing polymer to a blender tub comprising water from the water source.

16. The method of claim 1 further comprising determining the ion concentration of the water source based in part with an equilibrium equation, wherein the equilibrium equation calculates ion concentration of the water source to the conductivity or density of the water source.

17. The method of claim 1 wherein the TDS concentration of the water source changes over a period of time between and during hydraulic fracturing stages.

18. The method of claim 1 wherein the at least one ion concentration is calcium ion, iron ion, or a combination thereof.

19. The method of claim 1 wherein the viscosity requirement is a function of an initial viscosity of the aqueous base fluid and a viscosity contribution of at least one friction reducing polymer.

20. The method of claim 1 wherein the correlating the TDS concentration of the water source to an ion concentration of the water source uses a calibration curve based in part on an input signal from water testing equipment.

* * * * *

UNITED STATES PATENT AND TRADEMARK OFFICE
CERTIFICATE OF CORRECTION

PATENT NO. : 10,988,675 B2  
APPLICATION NO. : 16/234178  
DATED : April 27, 2021  
INVENTOR(S) : Howard Thomas Riley, Teddy Joel Dubois and James William Ogle Page 1 of 1

It is certified that error appears in the above-identified patent and that said Letters Patent is hereby corrected as shown below:

In the Claims

Column 19 Lines 59-60, Claim 1 from "having a viscosity requirement measuring at least" to --having a viscosity requirement; measuring at least--.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*